(12) United States Patent
Reynolds et al.

(10) Patent No.: US 10,105,151 B2
(45) Date of Patent: Oct. 23, 2018

(54) INSTRUMENT FOR INTRA-OPERATIVE IMPLANT TEMPLATING USING FLUOROSCOPY

(71) Applicant: Wright Medical Technology, Inc., Memphis, TN (US)

(72) Inventors: David Reynolds, Lakeland, TN (US); Paul Stemniski, Arlington, TN (US); Richard Obert, Germantown, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 920 days.

(21) Appl. No.: 14/096,831

(22) Filed: Dec. 4, 2013

(65) Prior Publication Data

US 2014/0163563 A1  Jun. 12, 2014

Related U.S. Application Data

(60) Provisional application No. 61/736,323, filed on Dec. 12, 2012.

(51) Int. Cl.
*A61B 17/15* (2006.01)
*A61B 17/17* (2006.01)
*A61B 90/00* (2016.01)

(52) U.S. Cl.
CPC .......... *A61B 17/1717* (2013.01); *A61B 17/15* (2013.01); *A61B 17/1703* (2013.01); *A61B 17/1775* (2016.11); *A61B 2090/3966* (2016.02)

(58) Field of Classification Search
CPC ... A61B 17/17; A61B 17/1703; A61B 17/171; A61B 17/1717; A61B 17/1721; A61B 17/1725; A61B 17/1742; A61B 17/175; A61B 17/1753; A61B 2017/1775
See application file for complete search history.

(56) References Cited

U.S. PATENT DOCUMENTS

| 5,768,134 A | 6/1998 | Swaelens et al. |
| 7,083,624 B2 * | 8/2006 | Irving ............ A61B 17/157 |
| | | 606/87 |

(Continued)

FOREIGN PATENT DOCUMENTS

| GB | 2398011 A | 8/2004 |
| GB | 2402883 A | 12/2004 |

(Continued)

OTHER PUBLICATIONS

First Office Action issued for Chinese patent application No. 201310681872.4, dated Sep. 6, 2015, 10 pages.

(Continued)

*Primary Examiner* — Kevin T Truong
*Assistant Examiner* — Tracy Kamikawa
(74) *Attorney, Agent, or Firm* — Duane Morris LLP

(57) ABSTRACT

A surgical instrument having a first assembly with a first radio-opaque portion providing a profile of a first portion of an intramedullary implant or canal in a bone, and a second assembly having a second radio-opaque portion providing a profile of a second portion of the intramedullary implant or canal. The surgical instrument may also include a third radio-opaque portion providing an alignment feature to provide a fluoroscopic planar check for the surgical instrument.

13 Claims, 4 Drawing Sheets

(56) References Cited

U.S. PATENT DOCUMENTS

| | | | |
|---|---|---|---|
| 7,534,246 B2* | 5/2009 | Reiley | A61B 17/15 606/96 |
| 9,033,987 B2 | 5/2015 | Hanson et al. | |
| 2006/0229730 A1 | 10/2006 | Reiley et al. | |
| 2011/0125200 A1* | 5/2011 | Hanson | A61B 17/1764 606/86 R |

FOREIGN PATENT DOCUMENTS

| | | |
|---|---|---|
| JP | H08-505560 A | 6/1996 |
| JP | 2005-237527 A | 2/2004 |
| JP | 2009-148597 A | 7/2009 |
| JP | 2011-172614 A | 9/2011 |
| WO | 95/13018 A1 | 5/1995 |
| WO | 2008/017501 A1 | 2/2008 |
| WO | 2008155772 A1 | 12/2008 |
| WO | 2011072249 A1 | 6/2011 |
| WO | 2011/154891 A2 | 12/2011 |
| WO | 2012007054 A1 | 1/2012 |
| WO | 2012/162608 A1 | 11/2012 |

OTHER PUBLICATIONS

Search report for EP 13196779 dated Feb. 25, 2014.
Communication issued in connection with corresponding European patent application No. 13196779.6, dated Aug. 4, 2016 4 pages.

* cited by examiner

INSTRUMENT FOR INTRA-OPERATIVE IMPLANT TEMPLATING USING FLUOROSCOPY

FIELD OF DISCLOSURE

This application is a non-provisional of U.S. Patent Application No. 61/736,323, which was filed Dec. 12, 2012, the entirety of which is incorporated by reference herein.

The disclosed system and method generally relate to surgical guides and instruments. More specifically, the disclosed system and method relate to surgical guides and instruments for orthopedic procedures.

BACKGROUND

Total joint replacement prostheses typically include a specially designed jig or fixture to enable a surgeon to make accurate and precise bone resections in and around the joint being prepared to accept the prosthesis. The ultimate goal with any total joint prosthesis is to approximate the function and structure of the natural, healthy structures that the prosthesis is replacing. Should the prosthesis not be properly attached to the joint or not properly aligned, discomfort to the patient, gait problems, or degradation of the prosthesis may result.

Many surgical procedures employ the use of intra-operative fluoroscopy to check the alignment of the intramedullary cavities that are prepared to receive the joint replacement prosthesis; however, the use of intra-operative fluoroscopy may have drawbacks. One such drawback is that the use of fluoroscopy to check the alignment of intramedullary cavities formed during surgery may increase the overall length of the surgical procedure as time is taken to acquire and evaluate the fluoroscopic images. Long surgery times may lead to increased tourniquet time for the patient and may therefore increase recovery time.

Another drawback of fluoroscopy is exposing the patient and others in the operating room to the ionized radiation. For example, the U.S. Food and Drug Administration ("FDA") has issued several articles and public health advisories concerning the use of the fluoroscopy during surgical procedures. Consequently, even though steps are taken to protect the patient and other from the ionized radiation, it is virtually impossible to eliminate all risk associated with the ionized radiation.

Thus, it is desirable to overcome the limitations of the prior art and provide an efficient fluoroscopic check of the implant or prostheses and/or of the intramedullary cavities with or without the assistance of a preoperative plan or assessment.

SUMMARY

One embodiment of the present subject matter provides a surgical instrument having a first assembly with a first radio-opaque portion providing a profile of a first portion of an intramedullary implant or canal in a bone, and a second assembly with a second radio-opaque portion providing a profile of a second portion of the intramedullary implant or canal. These portions of the intramedullary implant may represent the stem of a prospective implant.

Another embodiment of the present subject matter provides a surgical instrument having a first module with a first radio-opaque portion providing a profile for an intramedullary implant or canal in a bone, and a second module with a second radio-opaque portion providing a profile for the intramedullary implant or canal in the bone. These first and second modules may provide an alignment check for the implant in two different planes. Further, any one or both of the first and second modules may include a first assembly having a third radio-opaque portion providing a profile of a first portion of an intramedullary implant or canal in a bone, and a second assembly having fourth and fifth radio-opaque portions, the fourth radio-opaque portion providing an alignment feature for the surgical instrument and the fifth radio-opaque portion providing a profile of a second portion of the intramedullary implant or canal whereby the third, fourth and fifth radio-opaque portions are subsets of the respective first and second radio-opaque portions.

An additional embodiment of the present subject matter provides a surgical instrument including a first assembly with a first radio-opaque portion providing a profile of a first portion of an intramedullary implant or canal in a bone, and a second assembly with a second radio-opaque portion providing an alignment feature for the surgical instrument.

These embodiments and many other objects and advantages thereof will be readily apparent to one skilled in the art to which the invention pertains from a perusal of the claims, the appended drawings, and the following detailed description of the embodiments.

DETAILED DESCRIPTION

Figure 1:
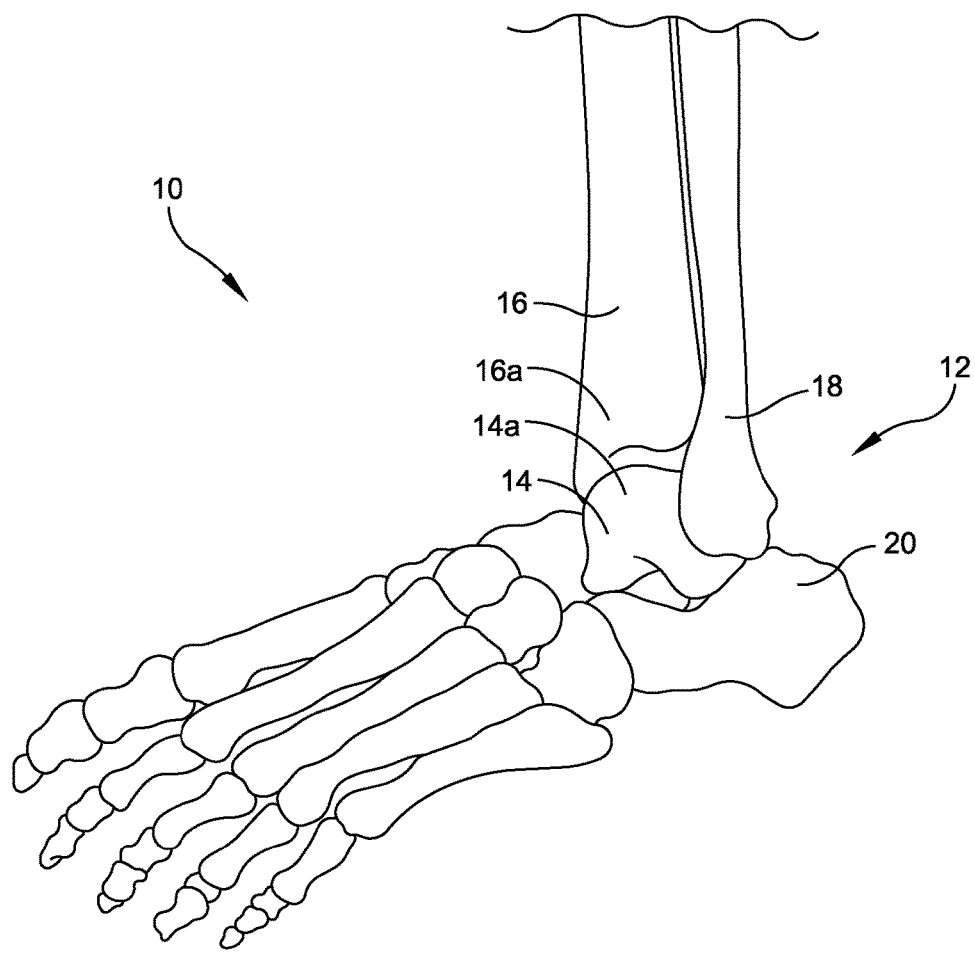
FIG. 1 is an illustration of the bones of a human foot and ankle.

With reference to the figures, where like elements have been given like numerical designations to facilitate an understanding of the present subject matter, the various embodiments of an instrument for intra-operative implant templating using fluoroscopy are described.

It should be noted that the figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

The disclosed systems and methods may advantageously utilize custom manufactured surgical instruments, guides, and/or fixtures that are based upon a patient's anatomy to reduce the use of fluoroscopy during a surgical procedure. These custom instruments, guides, and/or fixtures may be created by imaging a patient's anatomy with a computer tomography ("CT") scanner, a magnetic resonance imaging ("MRI") machine, or like medical imaging technology prior to surgery and utilizing these images to create patient-specific instruments, guides, and/or fixtures. This is generally termed as a preoperative assessment or plan and may be used in conjunction with intra-operative tools to accurately implement such a plan. Exemplary preoperative assessments or plans may allow a surgeon to specify the size, position and orientation of a patient's anatomical components and/or subsequent implant components within the joint or bone at issue based upon preoperative CT or MRI images. Of course, final component size and position may be determined intra-operatively through direct visualization by the surgeon with or without the aid of fluoroscopy.

Although the following description of the custom patient-specific instruments are described with respect to a foot 10 and ankle 12, one skilled in the art will understand that the systems and methods described herein may be utilized in connection with other joints and respective bones including, but not limited to, knees, hips, arms, shoulders, and the like. Thus, the claims appended herewith should not be so limited to an ankle and the bones associated therewith. As shown in FIG. 1, a typical human foot 10 includes an ankle joint 12 formed between a talus 14, which is disposed on a calcaneus 20, and a tibia 16 and fibula 18.

A CT or MRI scanned image or series of images may be taken of a patient's ankle 12 (or other joint and respective bones) and then converted from, e.g., a DICOM image format, to a solid computer model of the ankle including the calcaneus, talus, tibia, navicular, and fibula to determine implant alignment, type, and sizing using specialized modeling methods that are often embodied in computer software. Computer generated solid models that are derived from the data of the CT or MRI scan image will often include precise and accurate information regarding the surface contours surrounding the structures that have been imaged, e.g., the surface topography of the bones or contour of fascia that have been imaged. It will be understood that by surface topography it is meant the location, shape, size and distribution of surface features such as concavities and prominences or the like. The methods disclosed in U.S. Pat. No. 5,768,134, issued to Swaelens et al., which is incorporated by reference herein in its entirety, have been found to yield adequate conversions of data of CT or MRI scan images to solid computer models. In some embodiments, images are made of a foot 10, i.e., the calcaneus 20, talus 14, tibia 16, and fibula 18 of a patient using a CT or MRI machine, or other digital image capturing and processing unit as is understood by one skilled in the art and a model generated.

Figure 2:
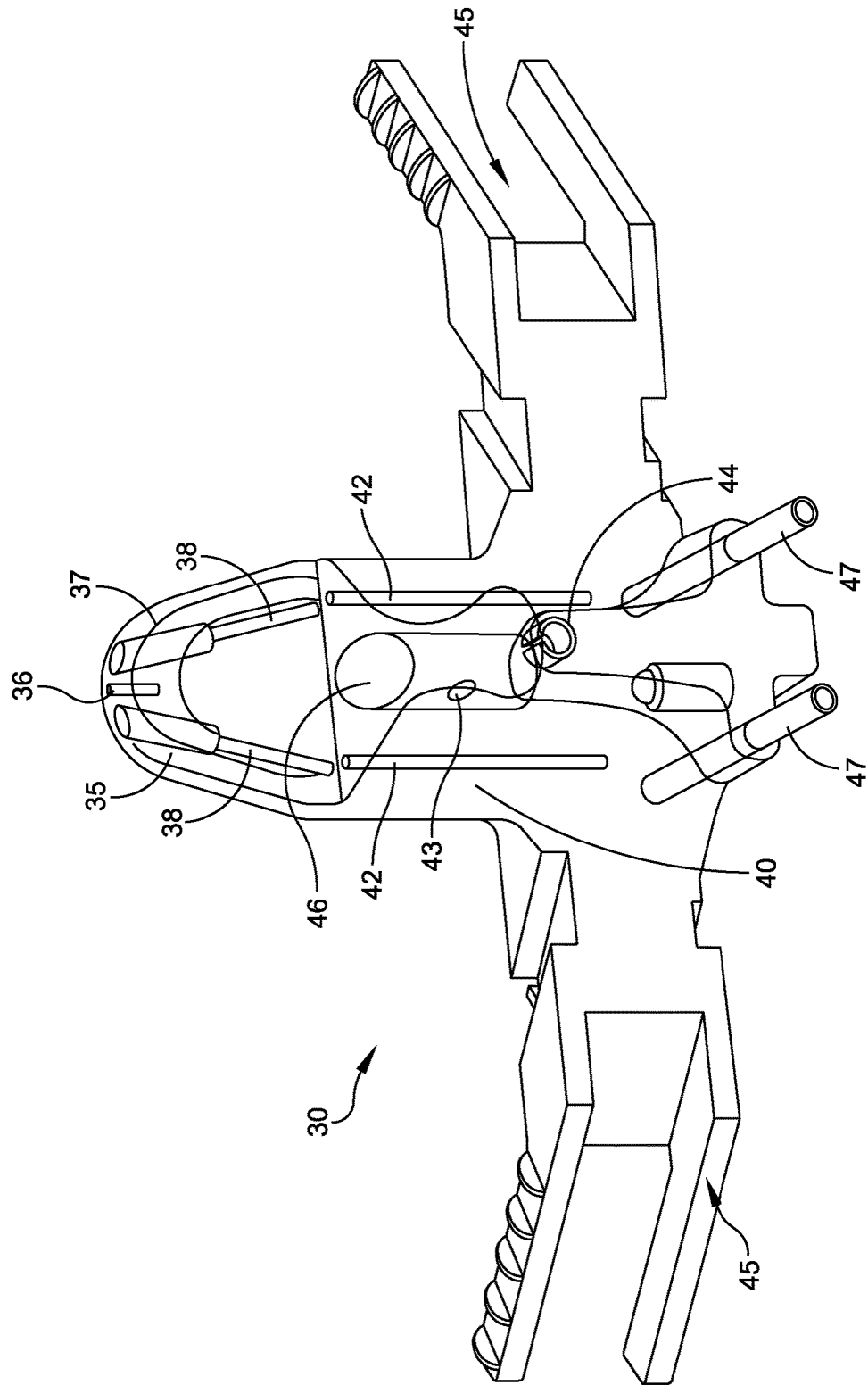
FIG. 2 is a perspective view of a surgical instrument according to one embodiment of the present subject matter.

FIG. 2 is a perspective view of a surgical instrument according to one embodiment of the present subject matter. With reference to FIG. 2, a surgical instrument 30 according to one embodiment of the present subject matter may be used in conjunction with patient-specific alignment guides to act as an intraoperative implant template. With such a template instrument attached to a patient-specific alignment guide and with the patient-specific alignment guide attached to the patient's anatomy, an exemplary instrument may be used to evaluate a prospective or resulting implant or prosthesis size, placement and orientation prior to committing to the location of the patient-specific alignment. Exemplary instruments according to embodiments of the present subject matter may be used in conjunction with a preoperative assessment of plan which may represent the planned location of a patient specific guide with fluoroscopic check features over the patient's CT or MRI scan derived anatomy for side-by-side comparison against intraoperative imaging. As illustrated, the surgical instrument 30 may include a first assembly 35 having both radiolucent 37 and radio-opaque portions 36, 38. These radio-opaque portions may be comprise of a metal or other radio-opaque material. These radio-opaque portions 36, 38 may also provide an alignment indication 36 of the assembly 35 and/or may provide a profile 38 of a first portion of a prospective or resulting intramedullary implant or canal for a bone (not shown). Exemplary bones may be, but are not limited to, the tibia, femur, humerus, radius, ulna, vertebrae, and fibula. Further, the provided alignment indication 36 may represent the position or alignment of a portion of the implant with a longitudinal axis of the bone, the position of a portion of the implant with a transverse axis of the bone, the position of a portion of the implant with a resection plane of the bone, a drill location for the bone, a drill orientation for the bone, and/or the position of a portion of the implant with an axis of the implant stem.

The surgical instrument 30 may also include a second assembly 40 having a second radio-opaque portion 30 which provides a profile 42 of a second portion of the prospective or resulting intramedullary implant or canal. In one embodiment, the first and/or second portions of the intramedullary implant may be the stem of the implant or may be the silhouette of the intramedullary canal accepting an implant. The second assembly 40 may also include a third radio-opaque portion 43, 44 which provides an alignment feature for the surgical instrument 30. Embodiments of the present subject matter may thus allow for intraoperative checks (e.g., fluoroscopic) in multiple planes to ensure proper positioning of implants, intramedullary canals, drill locations and the like. For example, one exemplary alignment feature may be a peg or rod 43 and a ring or cylinder 44 whereby the ring 44 substantially circumscribes the peg 43 upon planar alignment, e.g., Anterior-Posterior (A-P) alignment, of the instrument 30. Of course, such an alignment feature is exemplary only and the claims appended herewith should not be so limited as a myriad of alignment features using Kirschner wires, fiducial markers and other radio-opaque features may be employed by embodiments of the present subject matter. A further embodiment of the present subject matter may include a first assembly 35 having a first radio-opaque portion(s) 38 providing a profile of a first portion of an intramedullary implant in a bone and a second assembly 40 having only the radio-opaque portion 43, 44 which provides the planar alignment feature for the surgical instrument 30.

In another embodiment, the second assembly 40 may include a hole 46 or other attachment mechanism adaptable to attach an extra-medullary alignment rod (not shown) to the instrument 30. The surgical instrument 30 may include one or more lateral segments 45 that are adaptable to attach additional first assemblies and/or second assemblies thereto (see, e.g., FIG. 3). These additional first and second assemblies may thus provide a profile of the intramedullary implant or canal in a different and/or orthogonal plane (e.g., coronal, sagittal plane). Pegs, rods 47 or another attachment mechanism may be provided on or in the surgical instrument 30 for attaching a resection guide, drill guides and/or drill orientation guides thereto.

Figure 3:
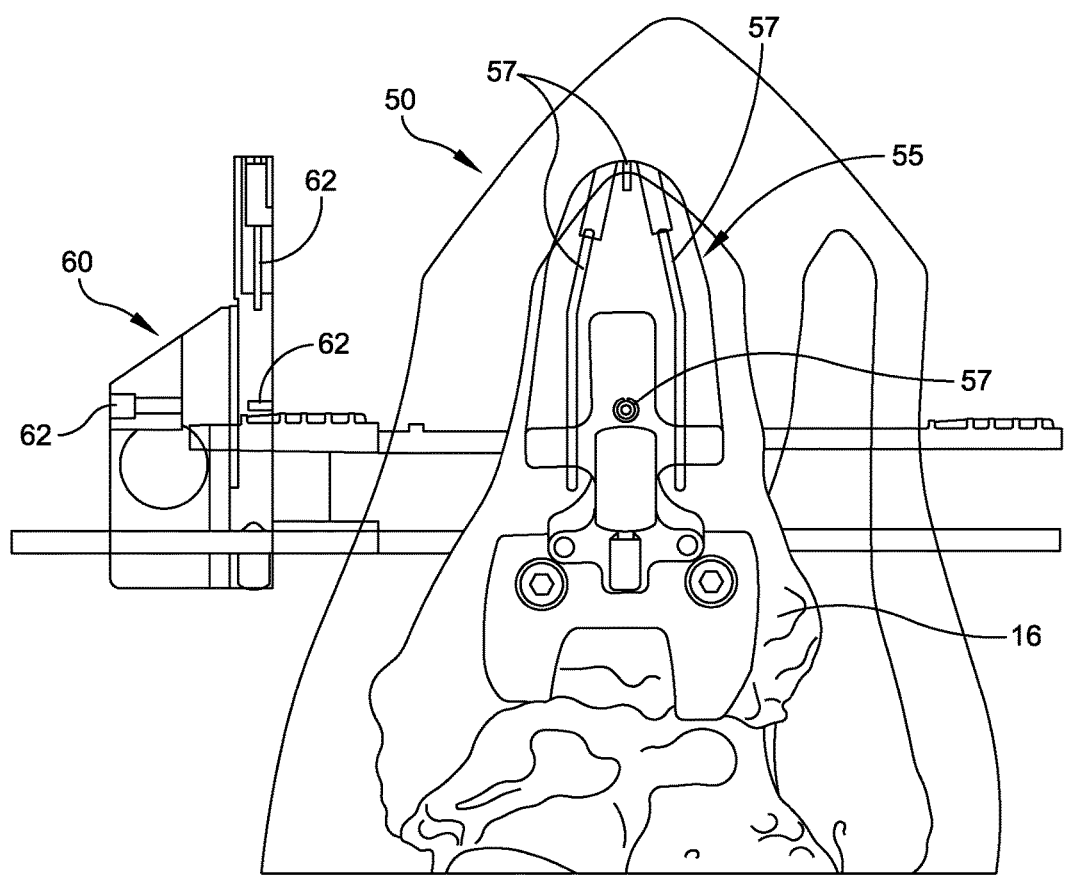
FIG. 3 is a front plan view of a surgical instrument according to another embodiment of the present subject matter.

FIG. 3 is a front plan view of a surgical instrument according to another embodiment of the present subject matter. With reference to FIG. 3, a surgical instrument 50 according to another embodiment of the present subject matter is illustrated attached to a tibia 16 and may include a first module 55 having a radio-opaque portion 57 providing a profile for a prospective or resulting intramedullary implant or canal for the tibia 16 (or other bone) and/or alignment features. The surgical instrument 50 may also include a second module 60 having a radio-opaque portion 62 providing a profile for the prospective or resulting intramedullary implant or canal in the bone and/or alignment features. As illustrated in FIG. 3, the first and second modules 55, 60 may provide an alignment check for the intramedullary implant or canal in two different planes (e.g., orthogonal, sagittal, coronal, etc.). With reference to FIG. 2, any one or both of the first and second modules 55, 60 illustrated in FIG. 3 may include first assemblies 35 having both radiolucent and radio-opaque portions whereby the radio-opaque portions may provide planar, linear or other alignment indications and/or may provide a profile of a first portion of an intramedullary implant or canal in the tibia 16. Of course, while a tibia 16 has been illustrated in FIG. 3, the claims appended herewith should not be so limited as it is envisioned embodiments of the present subject matter may provide a profile and/or alignment features for a prospective or resulting intramedullary implant or canal in the femur, humerus, radius, ulna, vertebrae, fibula, etc. Additionally, any one or both of the first and second modules 55, 60 may also include second assemblies 40 having radio-opaque portions which may provide a profile of a second portion of the intramedullary implant or canal and/or may provide an alignment feature for the surgical instrument 50. While an exemplary alignment feature may be a peg and a ring whereby the ring substantially circumscribes the peg upon planar alignment of the instrument 50, the appended claims herewith should not be so limited. As illustrated in the second module 60 of FIG. 3, the exemplary alignment feature consisting of a peg and ring may be laterally or longitudinally offset from each other to provide an adequate planar fluoroscopic alignment view or indication. Again, such an alignment feature is exemplary only and the claims appended herewith should not be so limited as a myriad of alignment features using Kirschner wires, fiducial markers and other radio-opaque features may be employed by embodiments of the present subject matter. Further, any one or both of the modules 55, 60 may also include resection guides, drill guides, drill orientation guides. While not shown, additional modules may also be included on an exemplary instrument 50 via the lateral segments to provide additional alignment and/or profile features in other planes.

Figure 4:
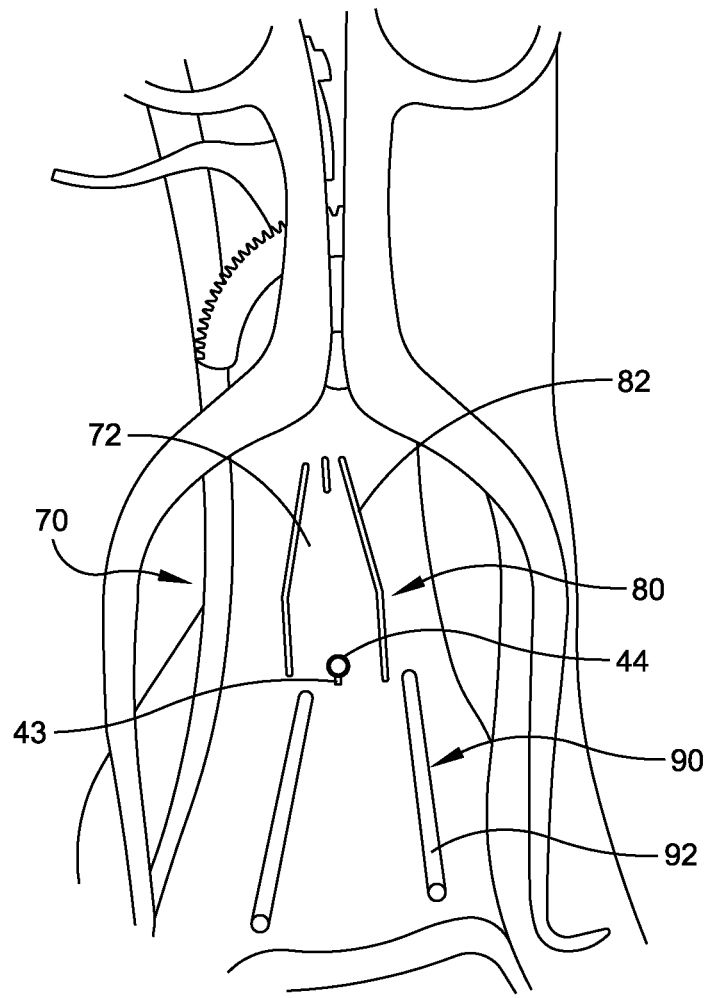
FIG. 4 is a fluoroscopic view of a surgical instrument according to one embodiment of the present subject matter in a non-aligned position.

FIG. 4 is a fluoroscopic view of a surgical instrument according to one embodiment of the present subject matter in a non-aligned position. With reference to FIG. 4, an exemplary surgical instrument 70 is shown illustrating misalignment of an intramedullary canal 72 through the lack of alignment of the radio opaque portions 82 of the first assembly 80 and the radio opaque portions 92 of the second assembly 90 during an intraoperative fluoroscopic check. Further, the surgical instrument 70 is shown in a non-aligned planar view as the ring or cylinder 44 does not substantially circumscribe the respective peg 43.

Embodiments of the present subject matter illustrated in FIGS. 2-4 and described above may be used to assist in obtaining a true view in the intended direction via a gunsight (e.g., circumscribed peg, fiducial markers, Kirschner wires, etc.) or alignment indication and may also provide an outline, silhouette, or overlay of one or more implants or intramedullary features. Such embodiments may allow for the attachment of other instruments that may assist in the physical alignment, sizing, pin placement, etc. of surgical guides and instruments (e.g., extra-medullary rod, drop rod, resection guides, drill guides, and the like). These exemplary embodiments may be used to ensure that an implant, such as a tibial implant may be properly inserted, aligned, and implanted into a respective tibia by conventional means including the removal of bone material from the tibia, fibula and/or talus using chisels, screws, drills, reamers and other conventional removal tools. The tibia, fibula and/or talus may then be sized, reshaped and/or resected to accept appropriate talar, tibial and/or fibular fixtures or implants. These fixtures may be mechanically affixed to the respective bone by screws, nails, bone cement and the like and may have surface-matched shapes specific to a patient's anatomy. One exemplary implant may be, but is not limited to, a Wright Medical Technologies, Inc. INBONE® total ankle system. The tibial implant may include a laterally extending tray or base shaped to conform to the patient's distal tibia after the distal portion of the tibia has been appropriately shaped and resected. The tibial implant or prosthesis may also include a stem or plug, sectioned or otherwise, extending generally perpendicular to a plane formed by the tibial base. The stem may be placed in a surgically formed opening extending into a patient's intramedullary canal. A plastic, polymeric insert may also be attached to the tibial base which provides a tibial articulating surface that articulates with the movement of the respective joint. A non-limiting, exemplary system and method for an ankle replacement is described in co-pending U.S. application Ser. No. 13/330,091 filed Dec. 19, 2011 and U.S. application Ser. No. 12/711,307, filed Feb. 24, 2010, the entirety of each being incorporated herein by reference.

Although reference has been made to a patient's talus, tibia, fibula, and ankle joint, one skilled in the art will understand that embodiments of the present subject matter may be implemented for other joints and respective bones including, but not limited to, the knee, hip, shoulder, or other joints. Thus, the disclosed devices and methods may advantageously utilize custom manufactured surgical instruments, guides, and/or fixtures that are based upon a patient's anatomy to reduce the use of fluoroscopy during a surgical procedure for a multitude of joints and respective bones.

One aspect of embodiments of the present subject matter is to provide a modular instrument to be used in conjunction with patent-specific alignment guides to act as an intraoperative implant template. With such a template instrument attached to a patient-specific alignment guide and with the patient-specific alignment guide attached to the patient's anatomy, an exemplary instrument can be used to evaluate the prospective or resulting implant size, placement and orientation prior to committing to the location of the patient-specific alignment.

A further aspect of embodiments of the present subject matter may assist in obtaining a true view in the intended direction of implantation via various alignment features and may also provide the outline, silhouette, or overlay of one or more implants or intramedullary cavities in one or more planes. A further aspect of certain embodiments may allow for the attachment of other instruments that may assist in the physical alignment, sizing, pin placement, etc. of surgical guides and instruments (e.g., extra-medullary rod, drop rod, resection guides, drill guides, and the like). Such aspects of embodiments of the present subject matter may be used in conjunction with a preoperative assessment or plan to provide for proper implantation and alignment of prostheses in a patient.

It may be emphasized that the above-described embodiments, particularly any "preferred" embodiments, are merely possible examples of implementations and merely set forth for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure and the present disclosure and protected by the following claims.

While this specification contains many specifics, these should not be construed as limitations on the scope of the claimed subject matter, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

As shown by the various configurations and embodiments illustrated in FIGS. 1-4, an instrument for intraoperative implant templating using fluoroscopy has been described.

While preferred embodiments of the present subject matter have been described, it is to be understood that the embodiments described are illustrative only and that the scope of the invention is to be defined solely by the appended claims when accorded a full range of equivalence, many variations and modifications naturally occurring to those of skill in the art from a perusal hereof.

What is claimed is:

1. An instrument, comprising:
   a body formed from a radiolucent material, the body including a patient-specific surface having a geometry that is complementary to at least a portion of a first bone of a patient;
   a first set of radio-opaque members disposed in the radiolucent body, a first member of the first set of radio-opaque members elongate from a respective first end to a respective second end along a first longitudinal axis, and a second member of the first set of radio-opaque members elongate from a respective first end to a respective second end along a second longitudinal axis, the first and second longitudinal axes extending in a superior/inferior direction, such that the first set of radio-opaque members collectively define a first profile that corresponds to an outline shape of a first portion of an orthopedic implant over which the instrument is overlaid; and
   a second set of radio-opaque members disposed in the radiolucent body, a first member of the second set of radio-opaque members elongate from a respective first end to a respective second end along a third longitudinal axis, and a second member of the second set of radio-opaque members elongate from a respective first end to a respective second end along a fourth longitudinal axis, such that the second set of radio-opaque members collectively define a second profile that corresponds to an outline shape of a second portion of the overlaid orthopedic implant, wherein the third and fourth longitudinal axes intersect to form an acute angle such that the first profile differs from the second profile and the second profile has a taper in a direction away from the first set of radio-opaque members.

2. The instrument of claim 1, wherein the body is coupled to an assembly, the assembly including at least one third radio-opaque member defining a profile that corresponds to a profile of the orthopedic implant in an anatomic viewing plane that is different from an anatomic viewing plane in which the first and second profiles of the orthopedic implant defined by the first and second sets of radio-opaque members are defined.

3. The instrument of claim 2, further comprising an alignment feature supported by the body, the alignment feature including a ring and a peg.

4. The instrument of claim 1, wherein the body defines a hole sized to receive an extra-medullary rod at least partially therein.

5. An instrument comprising:
   a radiolucent body including a first side having a patient-specific surface, the patient-specific surface having a geometry that is complementary to at least a portion of a first bone of a patient;
   a first set of radio-opaque members disposed in the radiolucent body, a first member of the first set of radio-opaque members elongate from a respective first end to a respective second end along a first longitudinal axis, and a second member of the first set of radio-opaque members elongate from a respective first end to a respective second end along a second longitudinal axis, the first and second longitudinal axes extending in a superior/inferior direction, such that the first set of radio-opaque members collectively define a first shape that corresponds to an outline shape of a first portion of an implant over which the instrument is overlaid;
   a second set of radio-opaque members disposed in the radiolucent body, a first member of the second set of radio-opaque members elongate from a respective first end to a respective second end along a third longitudinal axis, and a second member of the second set of radio-opaque members elongate from a respective first end to a respective second end along a fourth longitudinal axis, such that the second set of radio-opaque members collectively define a second shape that corresponds to an outline shape of a second portion of the overlaid implant, wherein the third and fourth longitudinal axes intersect to form an acute angle such that the first shape differs from the second shape and the second shape has a taper in a direction away from the first set of radio-opaque members; and
   a third set of radio-opaque members disposed in the radiolucent body, the third set of radio-opaque members collectively defining an alignment feature of the instrument.

6. The instrument of claim 5, wherein the third set of radio-opaque members includes a peg and a ring.

7. The instrument of claim 6, wherein the ring circumscribes the peg when the instrument is properly aligned with a first anatomic viewing plane.

8. The instrument of claim 7, wherein the radiolucent body includes at least one lateral segment, the at least one lateral segment adapted to attach an assembly to the instrument.

9. The instrument of claim 8, wherein the assembly includes at least one radio-opaque member for providing an indication of alignment in a second anatomic viewing plane when the instrument is positioned on the patient.

10. The instrument of claim 9, wherein the second anatomic viewing plane is one of a sagittal plane and a coronal plane.

11. The instrument of claim 7, wherein the peg and the ring are configured to each be positioned on the anterior side of the first bone of the patient.

12. The instrument of claim 5, wherein the radiolucent body defines a hole through a portion of the radiolucent body sized to receive an extra-medullary rod at least partially therein.

13. The instrument of claim 5, wherein the first and second members of the first set of radio-opaque members are positioned parallel to each other, and wherein the first and second members of the second set of radio-opaque members are positioned in a non-parallel and non-collinear relationship with respect to each other and with respect to the first set of radio-opaque members.

\* \* \* \* \*